United States Patent [19]

McAninch

[11] Patent Number: 5,312,323

[45] Date of Patent: May 17, 1994

[54] DISPOSABLE THIGH SUPPORT RING

[75] Inventor: Thomas S. McAninch, Detroit, Mich.

[73] Assignee: Detroit Receiving Hospital & University Health Center, Detroit, Mich.

[21] Appl. No.: 835,617

[22] Filed: Feb. 13, 1992

[51] Int. Cl.$^5$ ............................................. A61F 5/00
[52] U.S. Cl. ........................................... 602/32; 5/621
[58] Field of Search .......................... 602/5, 32-36, 602/38-40; 5/612, 621-624

[56] References Cited

U.S. PATENT DOCUMENTS

| | | | |
|---|---|---|---|
| 2,260,216 | 10/1941 | Doyle | 602/23 |
| 3,274,998 | 9/1966 | Grier, Jr. | 602/23 |
| 3,502,071 | 3/1970 | Holly | 128/25 R |
| 3,762,405 | 10/1973 | DeGeorge | |
| 3,827,431 | 8/1974 | Pecorella | |
| 3,878,842 | 4/1975 | Goldberg | 602/40 |
| 4,265,230 | 5/1981 | Jordon | |
| 4,621,625 | 11/1986 | Powlan | 602/33 |
| 4,649,907 | 3/1987 | Whitehead et al. | |
| 4,848,326 | 7/1989 | Lonardo | |
| 4,882,798 | 11/1989 | Worsnop | 5/86.1 X |

OTHER PUBLICATIONS

Zimmer Product Encyclopedia, 1978, pp. F36-F37, F-38, F-39, F-40.
Richard's Orthpedic Catalog, 1981, pp. 44, 74.
Product Catalog entitled "Zimmer Traction Handbook", 6th Edition, Zimmer Corporation.

Primary Examiner—Richard J. Apley
Assistant Examiner—Linda C. M. Dvorak
Attorney, Agent, or Firm—Harness, Dickey & Pierce

[57] ABSTRACT

A thigh support or ischeal ring is removably attached to a leg splint such as a Thomas or other similar type of splint. The ring is formed of a rigid material having fastening means integrally formed therewith and is substantially covered by at least one layer of padding to prevent irritating contact with the patient's thigh region.

8 Claims, 2 Drawing Sheets

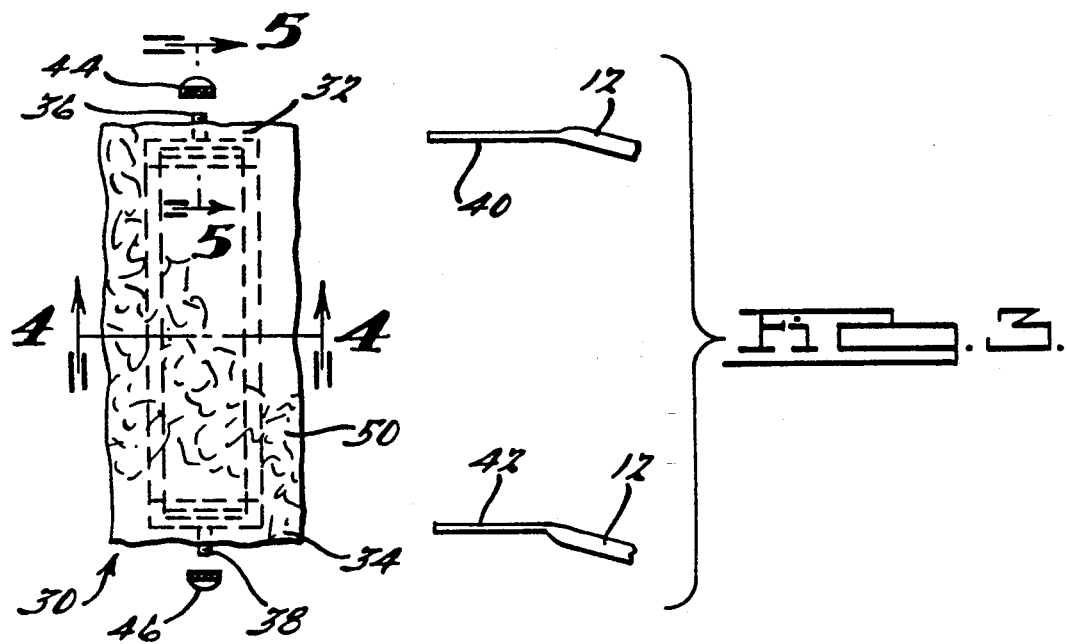
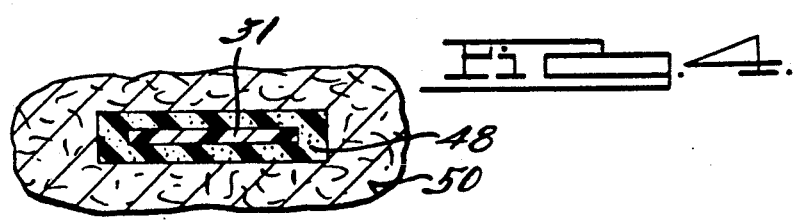
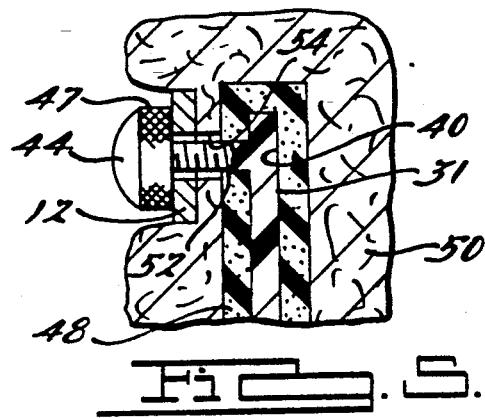

DISPOSABLE THIGH SUPPORT RING

FIELD OF THE INVENTION

This invention relates generally to traction splints which keep fractured bone parts in required alignment for healing and hold a broken limb in tension sufficient to ease the pain of fracture. More particularly, the present invention relates to a disposable padded ischeal or thigh support ring for a leg splint such as a Thomas splint.

BACKGROUND OF THE INVENTION

A typical traction arrangement employing a leg splint such as a Thomas or other similar type of splint is shown in FIG. 1. These splints generally include an elongated U-shaped section typically formed from metal tubing to which traction cords are attached, secured at each end to a thigh support ring, upon which a patient's thigh rests. The thigh support ring is most often formed of a rigid metallic or plastic material and is permanently mounted to the remaining U-shaped section splint. A pad or padding is usually placed by orthopedic personnel on or around the ring to prevent any irritating contact between the ring and a patient's thigh.

Typically, orthopedic personnel wrap the ring with a soft absorbent material prior to placing it under the patient's thigh. However, upon soiling such wrapping can be difficult to remove and replace without disturbing or disassembling the traction arrangement. Since it is imperative that such disturbance be minimized, orthopedic personnel often place absorbent towels between the wrapped ring and the patient's thigh, removing and replacing the towels when soiled. This method, however, is inadequate in that any soiling of the original wrap still remains and the wrap and towels may not sufficiently pad the ring or may bunch or unevenly pad the ring. While pads have been manufactured especially for these rings, pads employed to date have often been inadequate in size or design to cover and pad the entire ring, leading to some skin contact or points of pressure. These pads have also been difficult to remove for laundering or replacement while in use, causing unwanted disturbance in the traction set-up.

In practice, especially in cases of skeletal traction wherein a pin is placed through the fractured bone of the patient and traction forces are applied directly thereto, it is of utmost importance to disturb the traction arrangement as little as possible and to keep the area as sanitary as possible in order to prevent infection. Also, it is necessary to prevent uneven pressure points on the patient's limb as pressure sores, irreversible skin necrosis or even loss of limb may result.

SUMMARY OF THE INVENTION

The thigh support ring of the present invention makes such injury less likely and facilitates ease of use by orthopedic personnel by providing a ring which is readily removable from the U-shaped portion of the splint. This ring is also pivotally mountable thereto to assure maximum patient comfort and can be used on either the right or left thigh by rotation of 180° prior to attachment. Finally, the ring of the present invention is padded, for use with or without additional pad means, and is made of relatively inexpensive materials so as to be disposable to maintain sanitary conditions.

Additional objects, advantages, and features of the present invention will become apparent from the following description and amended claims, taken in conjunction with the accompanying drawings.

BRIEF DESCRIPTION OF THE DRAWINGS

FIG. 3 is a plan view of the thigh support ring according to the teachings of the present invention, shown disassembled from the U-shaped portion of the splint.

FIG. 4 is a sectional view of the thigh support ring taken through line 4—4 of FIG. 3.

FIG. 5 is a sectional view of the thigh support ring taken through line 5—5 of FIG. 3.

DETAILED DESCRIPTION OF A PREFERRED EMBODIMENT

Figure 1:
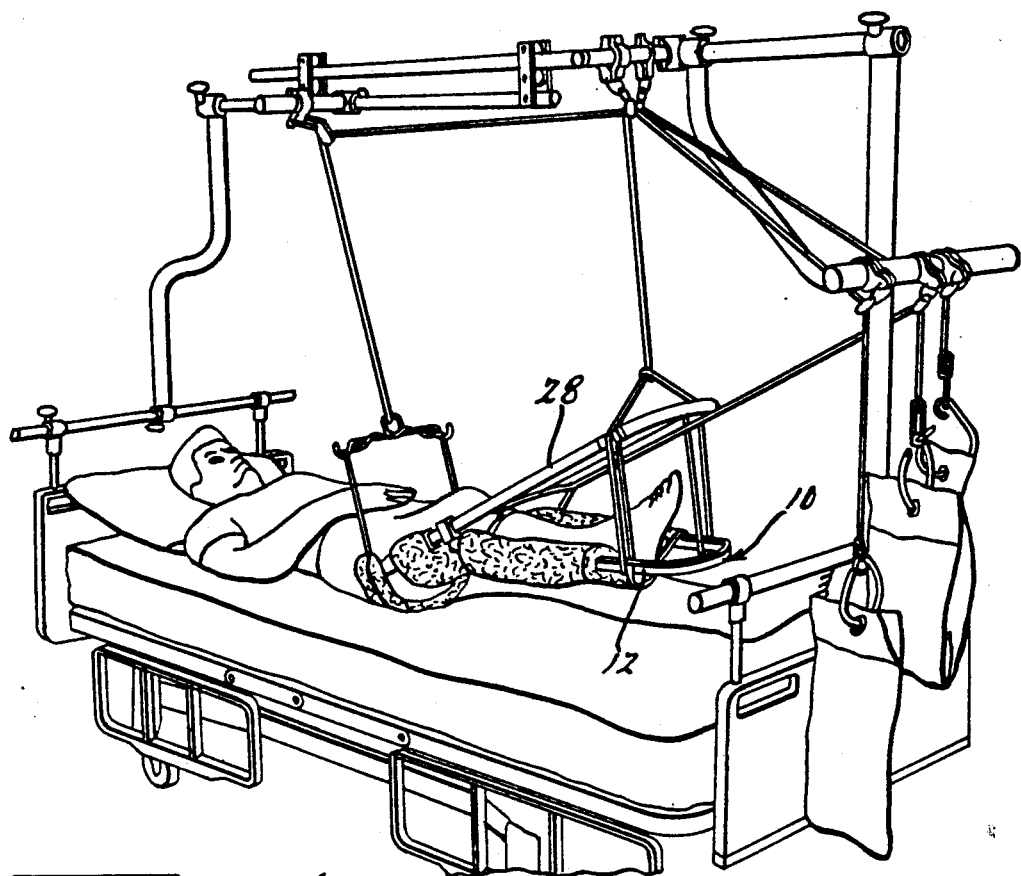
FIG. 1 is a pictorial view of a patient in traction with a leg splint such as a Thomas or other similar type of splint.
Figure 2:
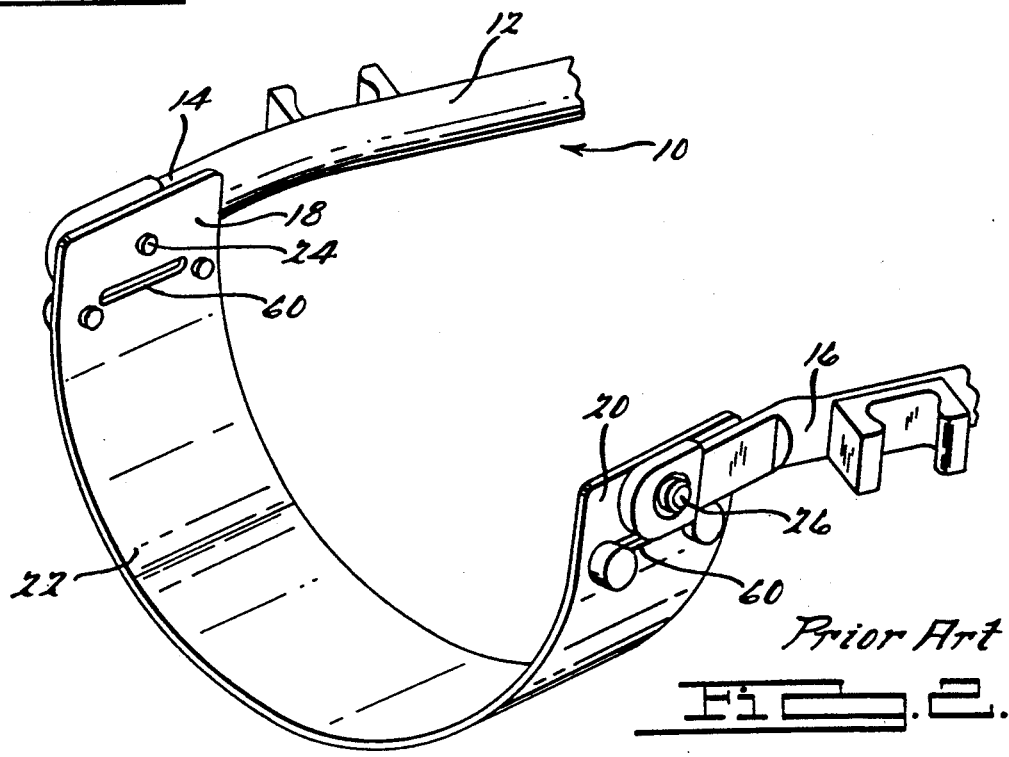
FIG. 2 is a partial perspective view of the splint showing a conventional thigh support ring in detail.

A typical leg splint 10 such as a Thomas splint is shown generally in FIGS. 1 and 2 and consists of an elongated U-shaped portion 12 which is conventionally attached (as shown best in FIG. 2) at ends 14, 16 thereof to ends 18, 20 of a thigh support ring 22 by fasteners such as rivets 24, 26 or the like. The U-shaped portion 12 of splint 10 is typically formed of lightweight metal tubing typically flattened at ends 14, 16 and may also be radiolucent. Conventional ring 22 is generally a rectangular piece of metal or plastic bent into a slightly skewed C-shape, the exact shape being dependent upon whether it is to be used in conjunction with traction of the right or left leg. A Pearson attachment 28 may or may not also be used in conjunction with splint 10 in order to produce a balanced suspension system as is shown in FIG. 1.

A readily removable, disposable ring for a splint according to the teachings of the present invention is shown generally at 30 in FIG. 3. The support ring 30 has an inner ring member 31 which is preferably formed of a rigid plastic material. Inner ring member 31 is generally rectangular in shape and bent or curved into a skewed C-shape. On each of sides 32 and 34 of ring member 31 are disposed fasteners 36, 38 for removably securing ring 30 to the splint 10. These fasteners preferably are male threaded members integrally formed with inner ring member 31. Alternately, however, fasteners 36, 38 may be separately formed bolts which pass through corresponding apertures formed in ring 30 or may be snaps or any other suitable fastening means. To ensure patient comfort and prevent any irritating contact of fasteners 36, 38 with the patient's thigh, fasteners 36, 38 are preferably formed so as to be flush with the interior surface 40 of inner ring member 31, or that surface of ring 30 toward the thigh when the splint and ring are in place.

Fasteners 36, 38 are positioned so as to pass through holes 40, 42 formed in the elongated U-shaped portion 12 of the splint 10 and receive opposing securing fasteners 44, 46, preferably female threaded cap screws. These cap screws 44, 46 preferably have a smooth rounded surface and a rough or scored region 47 to enable screwing onto fasteners 36, 38 by hand with a minimum of effort and without the need for tools.

To adequately pad ring 30, to prevent skin irritation as well as points of undesirable uneven pressure, inner ring member 31 is preferably covered with a thin padding 48, ideally a 0.25 inch sheet of foam which has been securely attached, such as by gluing, to surfaces of ring member 31 and wrapping therearound. Preferably the thin padding 48 is covered with a thick cushioning padding 50 such as natural or synthetic Kodel ® sheepskin pile. Cushioning padding 50 further ensures patient comfort and prevents the need for further pad means such as towels or other removable sheepskin pads as are commonly used by orthopedic personnel to pad the conventional thigh support ring 22. Both thin padding 48 and thick cushioning pad 50 substantially cover all portions of ring 30, leaving only openings 52, 54 to allow connection of fasteners 36, 38 to cap screws 44, 46. Fasteners 36, 38, therefore, are preferably of a length sufficient to allow protrusion beyond both padded layers 48, 50 and for subsequent fastening to cap screws 44, 46.

The padding layers 48 and 50 as well as inner ring member 31 are preferably made of relatively inexpensive materials, i.e., synthetic rather than natural sheepskin pile, so as to make the entire ring assembly 30 affordably disposable upon soiling or upon removal from the patient. Removability and disposability of the thigh support ring of the present invention provide several distinct advantages over the conventional fixed or riveted ring covered by removable or non-removable pads or towels.

The first advantage is the maintenance of sanitary conditions. Because the entire ring and padded layers are removed upon soiling, to be replaced with a new sterile ring, no soiled materials remain so as to be unsanitary or to cause any unpleasant odor. Also, upon removal of the ring from the splint, ready access is provided to the patient's thigh region for cleaning, massage or other care. Another advantage involves convenience for orthopedic personnel. The threaded cap screw arrangement is easy to secure and unsecure. Removal of the entire ring may also be easier than removing wrapping placed around pads or towels and saves laundering time and expense.

The foregoing discussion discloses and describes merely exemplary embodiments of the present invention. One skilled in the art will readily recognize from such discussion, and from the accompanying claims, that various changes and modifications can be made therein without departing from the spirit and scope of the invention as defined in the following claims.

What is claimed is:

1. A disposable thigh support ring for a leg splint, said leg splint having an elongated U-shaped section, said disposable support ring intended for one time only use in conjunction with said U-shaped section and adapted so as to be readily removable from and attachable to said U-shaped section, said disposable thigh support ring comprising:
    a rigid ring member being substantially rectangular in shape, curved generally into a C-shape, said ring member having an inside surface disposed toward a patient's thigh and an opposing outside surface;
    means for pivotally and removably fastening said ring member to said U-shaped section of said splint, said means for fastening comprising an outwardly projecting male threaded protrusion adapted to threadedly engage a female threaded cap screw, said male threaded protrusion being flush with said inside surface of said ring; and
    pad means permanently bonded to substantially all surfaces of said ring member to prevent contact of a patient's thigh region with said ring member, said pad means including a first layer comprising a sheet of foam permanently bonded to substantially all surfaces of said rigid ring member in a manner so as to prevent bunching and a second layer of sheepskin pile permanently bonded about said foam, said pad means further having at least one aperture formed therethrough to accommodate said male threaded protrusion.

2. The ring of claim 1 wherein said foam is approximately 0.25 inches thick.

3. The ring of claim 1 wherein said foam is bonded to said rigid ring member with an adhesive.

4. The ring of claim 1 wherein pile is formed of synthetic materials.

5. The ring of claim 1 wherein said pile is natural sheepskin.

6. The ring of claim 1 wherein said male threaded protrusion is integrally formed with said rigid ring member.

7. The ring of claim 1 wherein said U-shaped section of said splint includes a hole defined at each end thereof, and wherein said ends of said U-shaped section are placed exteriorly to said ring member, said male threaded protrusion passing through a corresponding hole in said U-shaped section.

8. A thigh support ring for a leg splint, said leg splint including an elongated U-shaped section, said U-shaped section having a hole formed at each end thereof, said support ring being disposable and intended for one time only use in conjunction with said U-shaped section, said disposable support ring being readily removable from and attachable to said U-shaped section and comprising:
    a rigid ring member being substantially rectangular in shape, curved generally into a skewed C-shape, said ring member having an inside surface disposed toward a patient's thigh and an opposing outside surface;
    means for pivotally and removably fastening said ring member to said U-shaped section of said splint, said means for fastening comprising a pair of outwardly projecting male threaded protrusions, said male threaded protrusions being flush with said inside surface of said rigid ring member, each said male threaded protrusion passing through one of said holes in said U-shaped section;
    a pair of female threaded cap screws, each adapted to threadedly engage one said male threaded protrusion; and
    pad means permanently attached to substantially all surfaces of said rigid ring member to prevent contact of a patient's thigh region with said rigid ring member, said pad means including a first layer comprising a sheet of foam adhesively bonded to substantially all surfaces of said ring member so as to prevent bunching thereof and a second layer of synthetic sheepskin pile attached about substantially all surfaces of said foam layer, said foam and pile pad layers having at least one aperture formed therethrough to accommodate said male threaded protrusion.

* * * * *